United States Patent [19]

Gross

[11] 4,220,920
[45] Sep. 2, 1980

[54] ELECTRODELESS CONDUCTIVITY MEASURING SYSTEM

[75] Inventor: Thomas A. O. Gross, Lincoln, Mass.

[73] Assignee: The Foxboro Company, Foxboro, Mass.

[21] Appl. No.: 24,554

[22] Filed: Mar. 28, 1979

[51] Int. Cl.² ............................................. G01N 27/07
[52] U.S. Cl. .................................... 324/442; 324/445; 336/84 C
[58] Field of Search ............... 324/442, 445; 336/84 C

[56] References Cited

U.S. PATENT DOCUMENTS

| 2,542,057 | 2/1951 | Relis ..................................... 324/445 |
| 2,869,071 | 1/1959 | Esterson .............................. 324/445 |
| 3,806,798 | 4/1974 | Gross .................................... 324/445 |

Primary Examiner—Alfred E. Smith
Assistant Examiner—Charles F. Roberts
Attorney, Agent, or Firm—John W. Ericson

[57] ABSTRACT

An electrodeless conductivity measuring system of the type employing a spaced pair of toroidal ferromagnetic cores, in which anomalies in the permeance of the cores is alleviated by the use of non-permeable shields of conductive material.

7 Claims, 4 Drawing Figures

ELECTRODELESS CONDUCTIVITY MEASURING SYSTEM

This invention relates to the determination of the conductivity of fluids, and particularly to novel electrodeless apparatus for determining the conductivity of fluids for measurement, testing and control.

The conductivity of a fluid is of interest for a wide variety of purposes; for example, as a measure of contaminants in drinking water, of the tendency for boiler water to deposit scale, and of the concentrations of industrial chemical process streams. Applications such as these involve the determination of conductivities over a very large range, and in many different environments. As an indication of the scope of the problem, the following table gives typical values and ranges of conductivity, in $ohm^{-1} \cdot cm^{-1}$, and reciprocal values of resistivity, in $ohm \cdot cm$, encountered in practice.

| Fluid | Conductivity | Resistivity |
|---|---|---|
| Absolute Water | $5.5 \times 10^{-8}$ | $18.3 \times 10^6$ |
| Distilled Water | $2 \times 10^{-7}$ | $5 \times 10^6$ |
| New Hampshire Mountain Stream | $10^{-5}$ | $10^5$ |
| City Tap Water | $5 \times 10^{-5}$ to $10^{-3}$ | 20000 to 1000 |
| Sea Water | .048 | 21 |
| Industrial Process Stream | 0.1 to 0.8 | 10 to 1.2 |

The extremely high conductivity of 0.8 $ohm^{-1} \cdot cm^{-1}$ is for a 19 percent solution of hydrochloric acid in water at 25° C. The value given for absolute water is theoretical.

With high resistance fluids, capacitance effects must be considered when the measurement is made with high frequency alternating current. The dielectric constant for water is 80; this corresponds to an apparent conductivity of $10^{-6} ohm^{-1} cm^{-1}$ at 25 kHz. Phase discrimination techniques must be used to obtain an accurate determination of the conductivity of distilled water, or of water purer than distilled water.

Conductivity measuring systems using electrodes in contact with the fluid whose conductivity is to be measured are employed to measure highly resistive fluids. But the accumulation of scale on the electrodes introduces errors, requiring frequent cleaning for accurate results. This is obviously a considerable drawback where it is desired to make frequent or continuous measurements, as in the control or monitoring of an industrial process. Accordingly, accurate electrodeless methods are in great demand.

It has long been known that the conductivity of a fluid, such as a liquid or a dispersion of solids in a liquid, can be determined by immersing a pair of insulated primary and secondary coils with toroidal ferromagnetic cores in the fluid, exciting the primary coils with alternating voltage, and sensing the voltage induced in the secondary coil as a measure of the conductivity of the fluid loop linking the cores. One form of apparatus for this purpose is described in U.S. Pat. No. 2,542,057, issued on Feb. 20, 1951 to M. J. Relis for Method and Apparatus for Measuring the Conductivity of an Electrolyte. As noted in that patent, the basic principle involved is that most of the flux induced in the primary coil is confined to its toroidal core. Thus, in the absence of a conductive link between the coils very little voltage will be induced in the secondary coil by the primary. However, as recognized by Relis, both electrostatic and electromagnetic stray and leakage fields cause spurious induced voltages in the secondary coil when the apparatus is arranged in the conventional manner, even though conventional thin split copper shields are placed over the coils, each coil is wound with a single turn loop cancelled by a return loop in the opposite direction, and one coil is rotated relative to the other to achieve minimum coupling.

In order to reduce these spurious voltages, Relis proposed to employ a compensating circuit that would add a voltage to the voltage induced in the secondary coil with an amplitude and phase that would cancel the spurious voltages. This solution has two disadvantages; one is the additional apparatus involved. The second, and more significant, is that the required compensating signal is not linear in the conductivity signal, because the spurious electromagnetic and electrostatic couplings are mutually affected by resistive leakage through the solution, and by the resistance of the solution to the flow of eddy currents, in such a way that calibration at a single point is inadequate to effect compensation. As a practical matter, apparatus of this type is useful primarily in the range of conductivities roughly above that of sea water, or 0.048 $ohm^{-1} \cdot cm^{-1}$.

One approach to the accurate measurement of conductivity with toroidal ferromagnetic coils and without external compensating networks is disclosed and claimed in my U.S. Pat. No. 3,806,798, issued on Apr. 23, 1974, for Electrodeless Conductivity Measuring System and assigned to the assignee of this application. In that patent, a circuit is disclosed in which the primary and secondary toroidal cores are each wound with a continuous winding that proceeds around the core in one direction, and then returns in the same direction, in such a way that electrostatic fields induced by spaced points on the coil at different potentials, and electromagnetic fields induced by a single winding progressing around the core, are cancelled. This approach has proven effective in minimizing coupling due to electrostatic effects and to all magnetic effects except those due to asymmetry in the permeable core material. With good cores, I have found it quite practical to extend the measuring range to conductivities down to about $10^{-4} ohm^{-1} \cdot cm^{-1}$. However, the feeble signals coupled by these high resistance fluids can be masked by the stray magnetic fluxes radiating from imperfect cores.

A perfect core would exhibit a zero external field, requiring that all sectors of the core have equal magnetic permeance. The effects of a local region of low permeability in the core material include radiation of flux from the primary, or transmitter, toroid, and imperfect cancellation of the external flux field in the secondary, or receiver, toroid.

While the simplest solution to the problem just mentioned would be to prescribe only the use of perfect cores, in practice, there are difficulties in securing such cores, particularly for use at the frequencies of most interest. In order to attain both smaller size and a better signal-to-noise ratio, electrodeless conductivity measuring systems are typically designed to operate at between 20 and 25 kHz. At lower frequencies, where a highly symmetrical core is desired, ring punchings are stacked to form a toroid with no discontinuities. Any preferred directions of magnetization can be cancelled by appropriately rotating the individual rings. This procedure is not inexpensive. Moreover, at 20 kHz the punchings should be only one mil in thickness, which is too thin to be practical.

Cores typically used in the 15 to 30 kHz range are made with Permalloy or Supermalloy tape wound into a ring and enclosed in a core box for protection. Some cores of this type are welded at the ends to prevent unwinding, and such should not be used for electrodeless conductivity measurements, as drastic local impairment of permeability occurs in the vicinity of the welds. However, other sources of asymmetry are less easily avoided. For example, the ends of the tape inherently introduce discontinuities, even though not welded to the cores, but secured by the core box. Also, improper fit of the core box can cause strains that will result in local degradation of permeability—when the core box is relied on to hold the tape in place, instead of a weld.

An extreme example of a local region of low permeability is an air gap or butt joint in the core structure. This would appear to be a highly undesirable feature in an electrodeless conductivity measuring system, but for some specialized applications it is necessary to use cores with butt joints to facilitate assembly.

Providing magnetic shielding around the winding, with permeable materials, would appear to be a practical expedient for the containment of flux in the primary toroid and prevention of stray pickup in the secondary. However, this approach introduces the problem of avoiding asymmetry in the shields. Such external shields are more exposed than the core, and thus are more subject to strain, giving rise to more local variations in permeability than the core.

It is the object of my invention to improve the accuracy with which conductivity can be determined by electrodeless methods, using toroidal cores having some local variations in permeability.

Briefly, the above and other objects of my invention are attained by the construction of an electrodeless conductivity probe comprising a pair of toroidal wound cores, on at least one of which there is an electrostatic shield of non-permeable, electrically conductive material extending partially around the core over at least the side facing the secondary core. A similar shield is preferred on the other core, extending partially around the core over at least the side facing the primary core. Preferably, the shield, or shields, is located under the winding for the associated core, rather than over the winding as in conventional shielding practice. It is also preferred that the thickness of the shield be determined, in a manner to be described below, as a function of the desired operating frequency of the system. For the measurement of low conductivities, it is preferred to employ the winding technique described in my above-cited U.S. Pat. No. 3,806,798. For the most exacting measurements, an auxiliary shield is provided, that is oriented oppositely to the main shield. The auxiliary shield should preferably be outside of the winding if the main shield is inside of the winding.

My invention will best be understood in the light of the following detailed description, together with the accompanying drawings, of various illustrative embodiments thereof.

Figure 1:
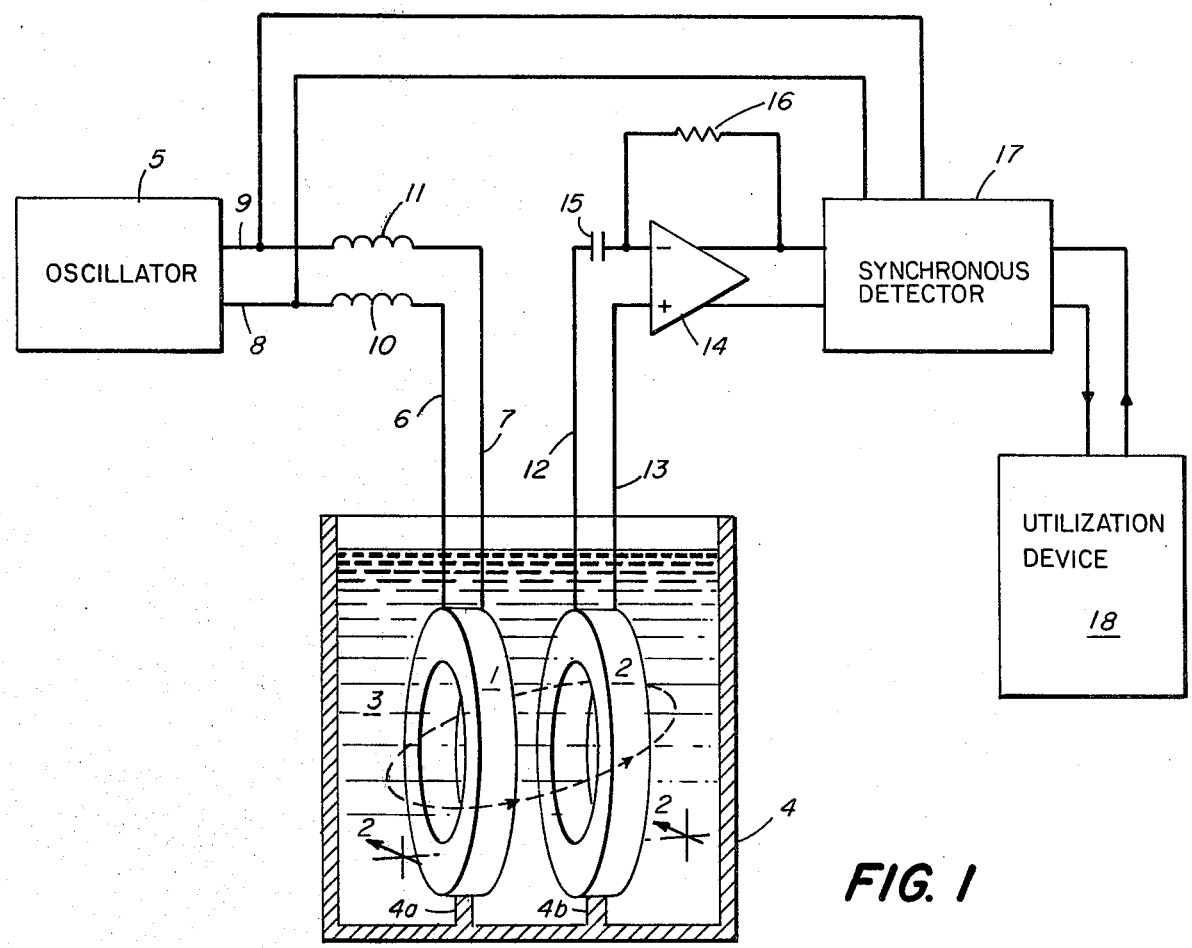
FIG. 1 is a schematic block and wiring diagram of an electrodeless conductivity measuring system in accordance with the invention, showing immersed transmitter and receiver coils in a perspective sketch with parts in cross section.
Figure 4:
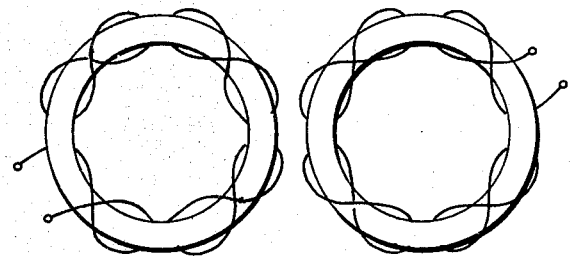
Figure 3:
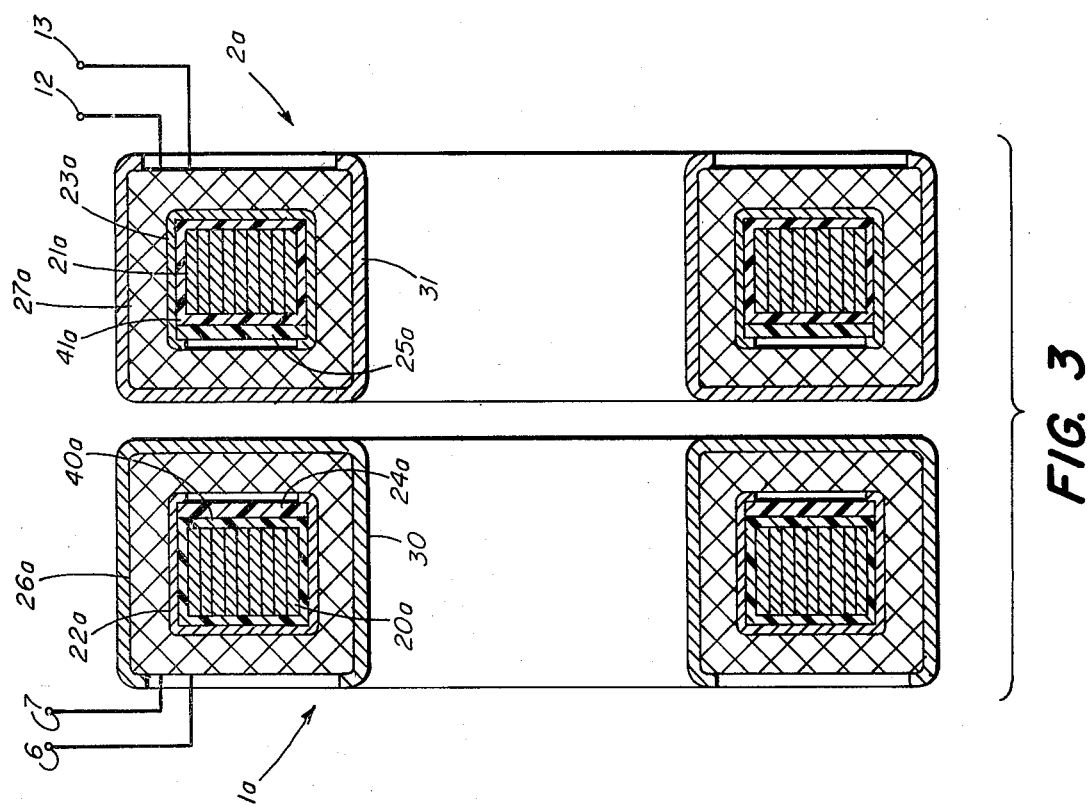
Figure 2:
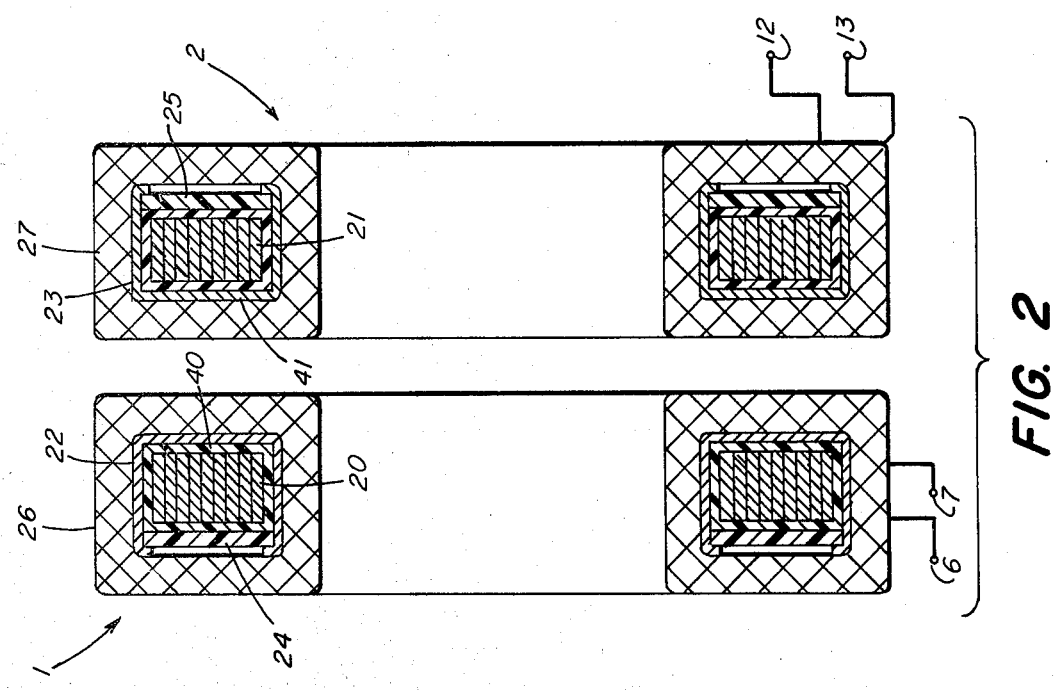
FIG. 2 is a schematic cross sectional view, on an enlarged scale, of the coils forming a portion of the apparatus of FIG. 1, in accordance with one embodiment of the invention, as seen essentially along the lines 2—2 in FIG. 1.

FIG. 3 is a view similar to that of FIG. 2, showing a modification of the invention; and FIG. 4 is a schematic wiring diagram of the preferred mode of winding the coils in the apparatus of FIGS. 1–3, which is per se prior art as described in my U.S. Pat. No. 3,806,798.

Referring to FIG. 1, I have shown an electrodeless conductivity measuring system that in all respects except those to be detailed below may be identical to that described in my U.S. Pat. No. 3,806,798, which is incorporated herein in its entirety by reference. As shown, the apparatus comprises a transmitter coil 1 and a receiver coil 2 immersed in spaced parallel relationship in a body of liquid 3 whose conductivity is to be measured. The liquid 3 is in a container 4 that may take any of the forms shown in my above cited U.S. Pat. No. 3,806,798. Means 4a and 4b, shown as formed integral with the container 4, are provided to mount the coils 1 and 2 in spaced parallel relationship.

The transmitter coil 1 is arranged to be excited by a conventional oscillator 5. The input to the coil 1 should be balanced with respect to ground. As shown in U.S. Pat. No. 3,806,798, this may be accomplished using a transformer with a secondary having a grounded center tap. However, a simpler, and therefore preferable, approach is shown in FIG. 1. As there shown, the terminals 6 and 7 of the coil 1 are connected to the output terminals 8 and 9 of the oscillator 5 by a pair of windings 10 and 11 comprising a conventional balun.

The coils 1 and 2 may each be wound in any conventional manner, but for exacting work are preferably wound in the manner described in U.S. Pat. No. 3,806,798.

The terminals 12 and 13 of the secondary, or receiver coil 2 are connected to a detecting circuit that may be of any conventional design. Preferably, however, the receiver coil is terminated in a virtual short circuit, in the manner described in more detail in my article, "Active Loads Improve Current Probe Performance", published in *EDN*, Jan. 5, 1978 issue on pages 94–96. As shown in FIG. 1, an operational amplifier 14 may be used as an active load termination for the coil 2, serving as a current to voltage converter. For this purpose, the terminal 13 of the coil 2 is connected to the non-inverting input terminal of the amplifier 14. The terminal 12 of the coil 2 is connected to the inverting terminal of the amplifier 14 through a coupling capacitor 15. The capacitor 15 serves to avoid undesirable d.c. offset. The amplifier 14 is provided with a conventional feedback resistor 16.

The output of the amplifier 14 can be connected to any conventional measuring, detecting or control circuit. However, if the electrically conductive shields for the coils 1 and 2 are constructed in the preferred manner described below, the output of the amplifier 14 is preferably connected to a synchronous detector 17. The synchronous detector 17 is synchronized with the oscillator 5, whose output terminals are connected to the synchronous detector 17, so that stray signal components in quadrature with the oscillator output are rejected. When the coil shields are made in the manner to be described, residual stray fields will be in quadrature with the oscillator output, and thus will not influence the output of the synchronous detector. A suitable sychronous detector is described in my article entitled, "Transformerless Synchronous Demodulator", that appears on page 13 of the mid-April 1978 issue of *Electronic Engineering*, published by Morgan-Grampian (Publishers) Limited, London, England.

The output signal from the synchronous detector 17 may be applied to any desired utilization device 18, such as any of the various measuring, detecting, or control circuits described in my above cited U.S. Pat. No. 3,806,798.

FIG. 2 shows the construction of the coils 1 and 2, in accordance with one embodiment of my invention, and in more detail. The cores of the coils may be of any desired ferromagnetic material, but are preferably of Permalloy or Supermalloy tape wound in spiral fashion as indicated at 20 for the transmitter coil 1 and at 21 for the receiver coil 2.

The spiral wound foils 20 and 21, respectively, for the coils 1 and 2, may be welded at the ends or contain butt joints or welds if so desired. However, for best results, the foils are not so joined, but are confined and contained by core boxes comprising highly conductive, but non-permeable partial shields 22, for the coil 1, and 23, for the coil 2, of material such as aluminum, copper, silver, or the like. The core boxes and shields 22 and 23 surround the cores 20 and 21 on three sides as shown in FIG. 1. Cores are supported in the boxes by oil, grease or a suitable resin or elastomer, indicated at 40 and 41, respectively, for the coils 1 and 2. The core boxes are completed by insulating discs 24 and 25, for the coils 1 and 2, respectively, of any suitable material such as nylon, a phenolic resin, an epoxy resin, any of the above or other resins filled with glass fibers, or the like.

In the embodiment of FIG. 1, it is necessary that the metal sides of the core boxes face each other, with the non-conducting sides of the core boxes facing away from each other, as shown, in order to obtain a substantial reduction in the effects of any core asymmetry that may be present. If the core boxes are oriented in the same direction, an intermediate degree of isolation is obtained. With the non-conducting sides 24 and 25 confronting each other, no improvement over non-conducting boxes has been found.

The coil 1 is provided with a winding 26 having as terminals the leads 6 and 7. Similarly, the coil 2 is provided with a winding 27 having as terminals the leads 12 and 13. The windings 26 and 27 may be of any conventional form, but as noted above, are preferably formed by winding continuously around the core in one direction for 360 degrees, and returning in the same direction back to the starting point, as many times as desired from one terminal to the other, as more fully described in my above cited U.S. Pat. No. 3,806,798.

Tape wound core constructions are usually supplied with non-conducting core boxes of nylon, phenolic resins, or glass-filled nylon for use at ordinarily encountered temperatures. Core boxes such as that comprising the metal portion 22 and the non-conducting portion 24 in FIG. 1, are occasionally used for high temperature environments, where the metal is usually aluminum and the non-conducting material is usually a glass-filled epoxy resin. However, these core boxes have been chosen for their environmental protection properties, without reference to any electrical effects.

It will be appreciated that the flux induced by the exciting current supplied to the winding 26 of the coil 1 is primarily confined to the core 20. Signals determined by the conductivity of the fluid 3 in the container 4 in FIG. 1 depend on the conductive path through the fluid 3 linking the coils 1 and 2. Spurious signals caused by discontinuities in the permeance of the core 20 of the coil 1 are for the most part reflected by the conductive portions 22 and 23 of the core boxes of the coils 1 and 2, and do not greatly perturb the signal induced in the winding 27 of the receiver coil 2. However, where hgih precision is required, where it is desired to measure very low conductivies, or where highly imperfect cores must be used, undesirably significant spurious signals may still be induced in the receiver coil. It has been found that these may be very drastically attenuated by the appropriate choice of the thicknesses of the conductive portions 22 and 23 of the core boxes of the coils 1 and 2, respectively.

Although it is well known that shields made of copper or other metals of high conductivity and negligible permeability are effective in shielding magnetic flux of high alternating frequency, it was not realized prior to the present invention that such shields could be effective in electrodeless conductivity probes operating below several hundred kiloHertz. While it is not desired to be bound by theory, as no adequate theoretical treatment of the problem has been found, it is thought that four basic factors contribute to the efficiency of non-permeable conductive shields when constructed and arranged in accordance with the invention.

Two factors that are clearly involved are the skin effect, and magnetic flux penetration into a conducting shield as limited by eddy current absorption. These matters are discussed by H. A. Wheeler in "Formulas for the Skin Effect", *Proceedings of the IRE*, Vol. 30, Sept. 1942. F. E. Terman, in *Electronic and Radio Engineering*, 4th Edition, McGraw-Hill Book Co. Inc., 1955, page 23, has adapted some of Wheeler's formulas to convenient engineering units. Terman shows that the skin depth $\delta$, where a current or flux at the surface of a conductor drops to $1/e$, where e is the base of the natural logarithm series, or 36.8 percent is given by:

$$\delta = 5033\sqrt{\rho/\mu f} \qquad (1)$$

where
$\delta$ = skin depth in centimeters
$\rho$ = resistivity of conductor, in ohm-centimeters
$f$ = frequency in Hertz
$\mu$ = relative magnetic permeability (for air, $\mu = 1$)
for copper at 20°, Equation (1) reduces to:

$$\delta = 6.62/\sqrt{f} \qquad (2)$$

A preferred material is aluminum, for which Equation (1) reduces to:

$$\delta = 8.17/\sqrt{f} \qquad (3)$$

In electrodeless conductivity measuring systems, f is typically 20 kHz, so that the skin depth in aluminum is approximately 0.058 cm., or about 22.7 mils.

A reduction in flux to 36.8 percent corresponds to 8.7 decibels. Eperiments made with electrodeless conductivity probes, in which care was taken to eliminate coupling effects due to magnetic flux from electrostatic causes, showed that an attenuation of magnetic flux on the order of 26 decibels was obtained with conductive shields 22 and 23 of aluminum 10 mils thick on each core. On the basis of absorption in the shields having a total thickness of 20 mils, an attenuation of only 7.7 decibels would be expected (8.7 db/22.7 mils=0.383 db/mil). Clearly, absorption of the flux is not the dominant factor in the isolation effected by shielding.

A third factor of which advantage is taken in accordance with a preferred embodiment of the invention for precise work is that the phase of flux transmitted through a non-permeable conductive shield is shifted in dependence on the thickness of the shield. If a phase quadrature rejection detecting circuit is employed as described above, and the combined thicknesses of the partial shields on the transmitter and receiver coils are selected so that the net phase log of the stray flux is 90° relative to the phase of the flux induced by coupling through the conductive fluid linking the transmitter and receiver coils, essentially complete rejection of the stray flux signal can be attained. However, while of great practical importance, this fact still does not completely explain the efficacy of the partial shields.

In the experiments with confronting shields of 10 mil aluminum discussed above, an attenuation of 26 db was observed. Comparing this result with theory, at the depth $\delta$ (defined above) in an aluminum shield, the phase of the flux will lag at the surface by one radian, or about 57.3°. Thus, given that the depth $\delta$ is 22.7 mils in aluminum, the phase lag in aluminum would be about 57.3°/22.7 mils=2.52°/mil. For the combined shield thickness of 20 mils, the phase lag would be 2.52×20, or 50.4°. The phase rejection factor at a lag of 50.4° is COS50.4=0.637, or only 3.9 db. This, plus the 7.7 db attenuation explained by absorption, still leaves 14.4 db. unaccounted for. It is convenient to explain this result by attributing the additional attenuation to reflection from the confronting metal shields, but, while there must be some attenuation due to this effect, it is not clear that still other factors are not present. In any event, the use of quadrature rejection detectors, together with appropriate shields yielding a 90° phase shift, is recommended. For aluminum, this would require transmitter and receiver shields with a combined thickness of 90°/2.52° mil=35.7 mils, or about 17.9 mils per shield if equal thicknesses are to be employed. Larger integral mutiples of these thicknesses may be employed if so desired; i.e., the net phase shift should preferably be $n\pi/2$, where n is any odd integer.

Shield thicknesses less than those just recommended may be employed, although thin electrostatic shields are not effective. A total shield thickness of at least $\delta$, as defined above, is desirable.

Referring to FIG. 3, a modification of the invention is shown which may be preferred for the most exacting work, where some of the preferred options discussed above are not exercisable, or simply for added environmental protection. The basic apparatus, comprising the cores 20a and 20b; the core boxes comprising non-permeable conducting portions 22a and 23a and non-conducting portions 24a and 25a; and the transmitter and receiver windings 26a and 27a, respectively, may be the same as the correspondingly numbered elements in FIG. 2. However, additional partial toroidal shields 30 and 31, of aluminum or other conductive, non-permeable material, preferably outside of the coils, are provided. In this embodiment, the conductive faces of the outer shields of each coil should face opposite the conductive faces of the inner shields of that coil, but it makes no difference in which direction the conductive face of one outer shield faces relative to the other. The coils should have their major dimensions parallel, however, as shown, for maximum efficiency and minimum stray coupling.

If desired, the auxiliary shields 30 and 31 in FIG. 3 ay be placed over the cores and under the windings 26a and 27a. Suitable electrical insulation must be provided between the shield 22a and the shield 30, and between the shield 23a and the shield 31, in this embodiment.

A significant advantage of the use of non-permeable shields in accordance with the invention, as compared with the use of permeable shields, is that a lack of symmetry in the non-permeable shields does not in itself result in undesired coupling between the primary (transmitter) coil and the secondary (receiver) coil. If a sector of the non-permeable shield has a high resistance relative to the rest of the shield for any reason, the effectiveness of the shield may be somewhat reduced, but a source of coupling is not introduced by the anomoly in resistance, as it would be in the case of an anomoly in permeance in a permeable shield.

At times, it may be necessary, as for reasons of assembly, to use toroidal cores that would not otherwise be chosen for use in electrodeless conductivity measuring systems, such as those having butt joints. Such may be employed with good results if relatively heavy dual shields of the type shown in FIG. 3 are employed, preferably with thicknesses chosen to cause any stray flux to be in quadrature with the flux coupled through fluid conduction, in combination with a quadrature rejecting detecting circuit as described above.

While my invention has been described with reference to the particular details of various illustrative embodiments, many changes and variations will become apparent to those skilled in the art upon reading this description, and such may obviously be made without departing from the scope of my invention.

Having thus described my invention, what I claim is:

1. An electrodeless conductivity probe, comprising first and second toroidal ferromagnetic cores, means mounting said cores in spaced relationship, a first and a second shield of electrically conductive, non-permeable material partially surrounding said first and said second cores, respectively, a first winding over said first shield and linking said first core, and a second winding over said second shield and linking said second core.

2. The apparatus of claim 1, in which said shields each comprise a partial toroidal core box extending around the associated core at least 180°, leaving an unshielded region not exceeding 180°, and a non-conductive element completing said core box and secured to said shield, and in which the shielded regions of said cores are in confronting relationship.

3. The apparatus of claim 1, further comprising means for applying a voltage at a predetermined frequency across said first winding, and means connected to said second winding for detecting a signal induced in said secondary winding by a conductive medium linking said cores.

4. The apparatus of claim 1, further comprising an oscillator connected to said first winding to apply an alternating voltage at a predetermined frequency to said first winding, and synchronous detection means connected to said oscillator and said second winding for producing an output signal in response to voltage induced in said second winding at said predetermined frequency and in a predetermined phase relative to said voltage applied to said first winding, said synchronous detecting means being non-responsive to voltages induced in said second winding at said predetermined frequency and displaced in phase by $n\pi/2$, where n is an odd positive integer, from said predetermined phase; said shields having a combined thickness such that flux passing through both shields at said predetermined frequency is shifted in phase by $n\pi/2$.

5. An electrodeless conductivity probe, comprising first and second toroidal ferromagnetic cores, means mounting said cores in adjacent spaced relationship, at least one shield of electrically conductive, non-permeable material partially surrounding at least a first of said cores and surrounding at least 180° of said first core on the side facing the other of said cores, and a winding on each of said cores.

6. The conductivity probe of claim 5, in which the total shield thickness is at least $\delta$, where $\delta = 5033\sqrt{\rho/\mu f}$, one of said cores is adapted to be excited at a frequency f Hertz, $\mu$ is the relative permeability of said material, and $\rho$ is the resistivity of said material in ohm·cm.

7. The conductivity probe of claim 3, in which the total thickness of said shields is at least $\delta$ cm., where $\delta = 5033\sqrt{\pi/\mu f}$, where $\pi$ is the resistivity of said shields in ohm·cm, $\mu$ is the relative permeability of said shields, and f is said predetermined frequency in Hertz.

* * * * *